United States Patent
Harrison et al.

(10) Patent No.: US 9,562,864 B2
(45) Date of Patent: Feb. 7, 2017

(54) CAVITY RESONATOR SYSTEM

(71) Applicant: Salunda Limited, Oxfordshire (GB)

(72) Inventors: Martin Roy Harrison, Northants (GB); Peter Wherritt, Oxfordshire (GB)

(73) Assignee: Salunda Limited, Oxfordshire (GB)

( * ) Notice: Subject to any disclaimer, the term of this patent is extended or adjusted under 35 U.S.C. 154(b) by 73 days.

(21) Appl. No.: 14/442,622

(22) PCT Filed: Nov. 19, 2013

(86) PCT No.: PCT/GB2013/053052
§ 371 (c)(1),
(2) Date: May 13, 2015

(87) PCT Pub. No.: WO2014/076506
PCT Pub. Date: May 22, 2014

(65) Prior Publication Data
US 2016/0123899 A1    May 5, 2016

(30) Foreign Application Priority Data

Nov. 19, 2012  (GB) .................................. 1220781.7
Nov. 19, 2012  (GB) .................................. 1220783.3
Jul. 31, 2013  (GB) .................................. 1313728.6

(51) Int. Cl.
*G01N 22/04*   (2006.01)
*H01P 7/04*    (2006.01)
(Continued)

(52) U.S. Cl.
CPC .......... *G01N 22/04* (2013.01); *G01N 33/2823* (2013.01); *G01N 33/2847* (2013.01); *H01P 7/04* (2013.01); *H01P 7/06* (2013.01)

(58) Field of Classification Search
CPC  G01N 22/04; G01N 33/2823; G01N 33/2847; H01P 7/04; H01P 7/06
See application file for complete search history.

(56) References Cited

U.S. PATENT DOCUMENTS 4,104,585 A    8/1978  Schofield

FOREIGN PATENT DOCUMENTS

GB  2376074 A   12/2002
GB  2400443 A   10/2004
(Continued)

*Primary Examiner* — David Gray
*Assistant Examiner* — Michael Harrison
(74) *Attorney, Agent, or Firm* — Honigman Miller Schwartz and Cohn LLP

(57) ABSTRACT

A cavity resonator system for measuring EM properties of the contents of a pipe portion comprises a primary resonator and a secondary resonator each with the same configuration comprising a conductive casing that defines a cavity and has openings for receiving a pipe portion, insulator material disposed inside the cavity, and antennae for generating and detecting a resonant EM field inside the cavity. In addition, the secondary resonator comprises at least one conductive screening ring that extends around the location occupied by a pipe portion for screening the interior of the ring from the field generated inside the cavity of the secondary resonator. By combining measures of parameters of the field from both resonators, the system may be used to generate a measure representative of EM properties of the contents of the pipe portion that is compensated for variation in the EM properties of the insulator material.

22 Claims, 8 Drawing Sheets

(51) Int. Cl.
*H01P 7/06* (2006.01)
*G01N 33/28* (2006.01)

(56) References Cited

FOREIGN PATENT DOCUMENTS

| GB | 2490685 A | 11/2012 | |
|---|---|---|---|
| GB | WO 2012172333 A1 * | 12/2012 | ............... G01F 1/66 |
| WO | WO-9004167 A1 | 4/1990 | |
| WO | WO-2012153090 A2 | 11/2012 | |

* cited by examiner

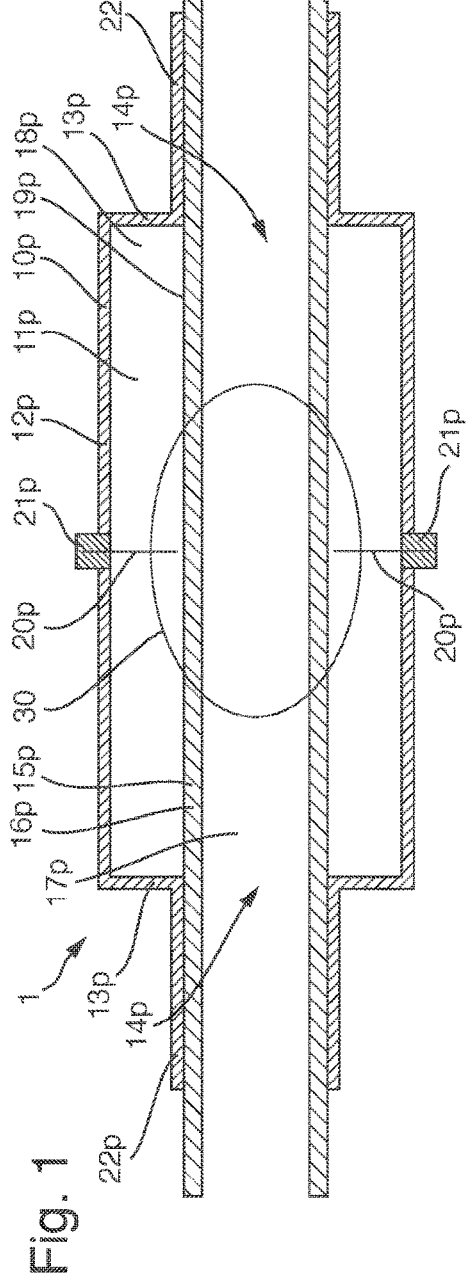
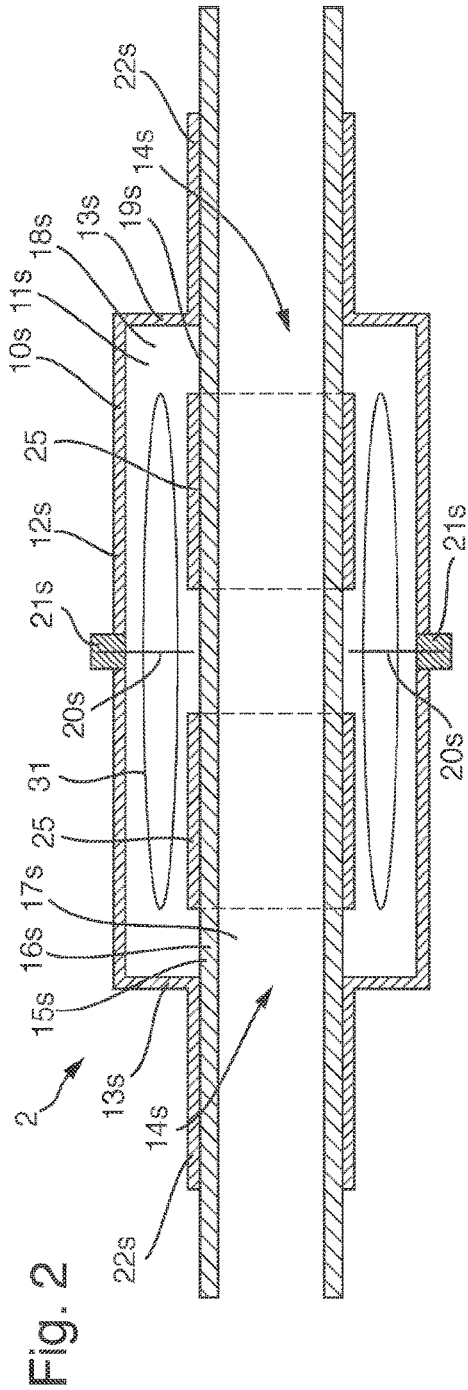

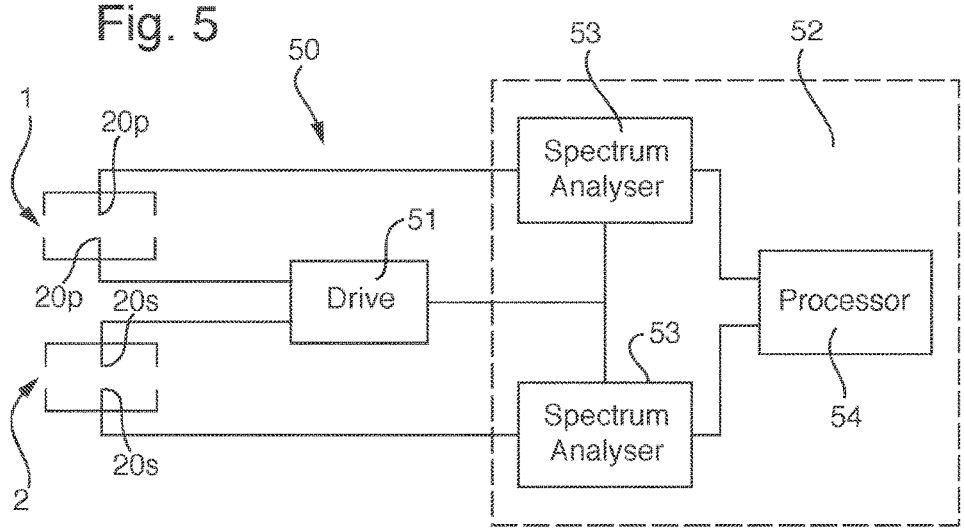
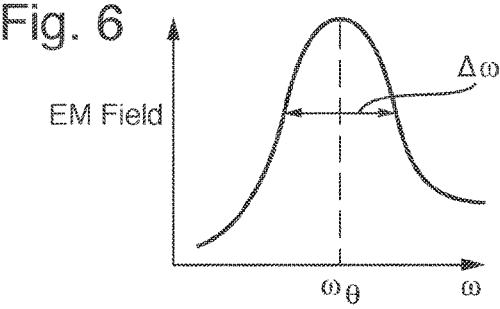
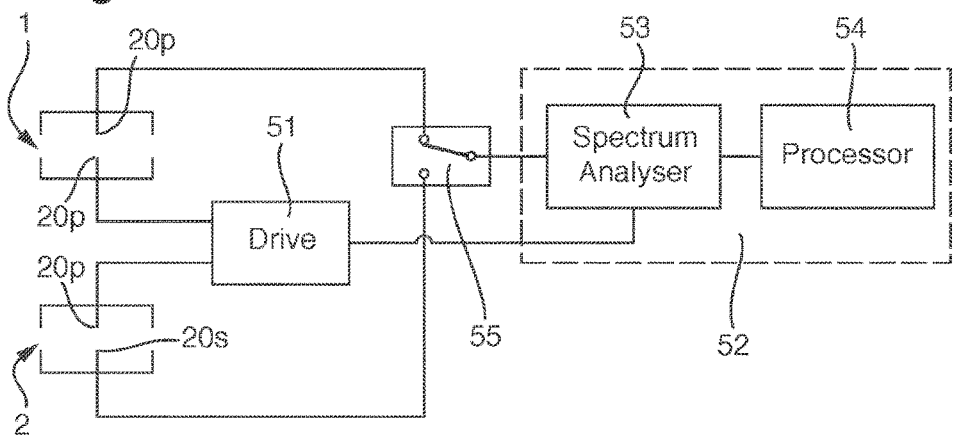

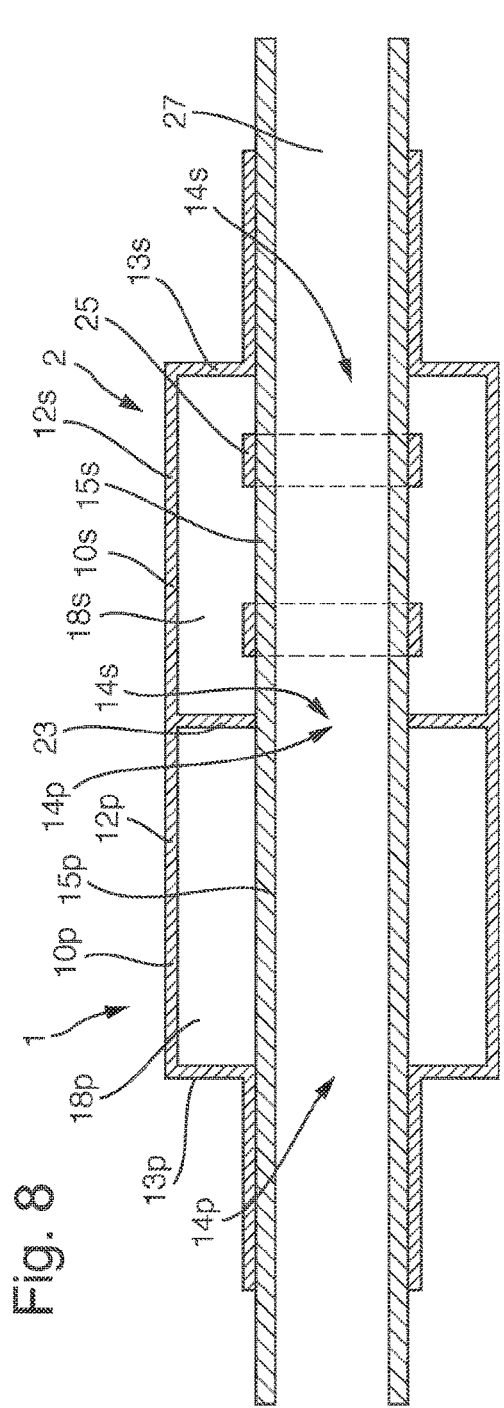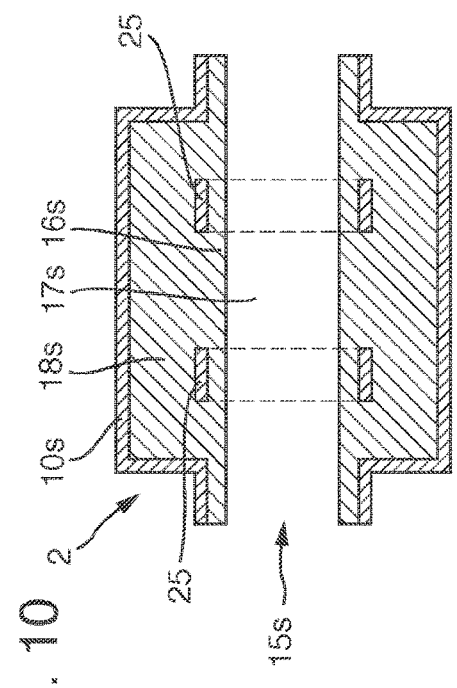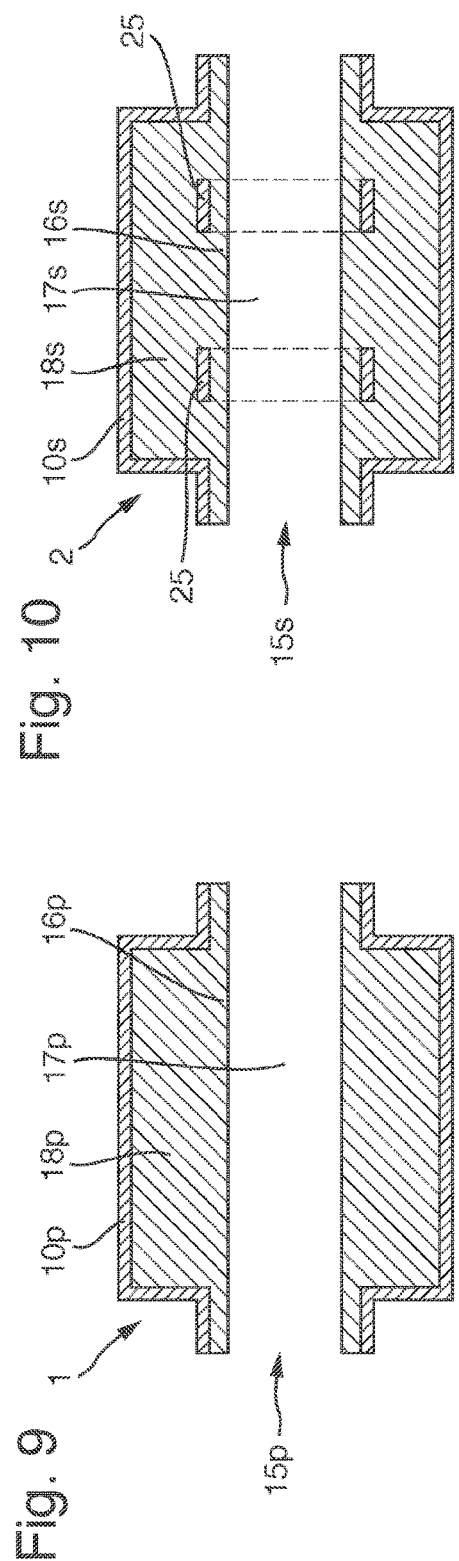

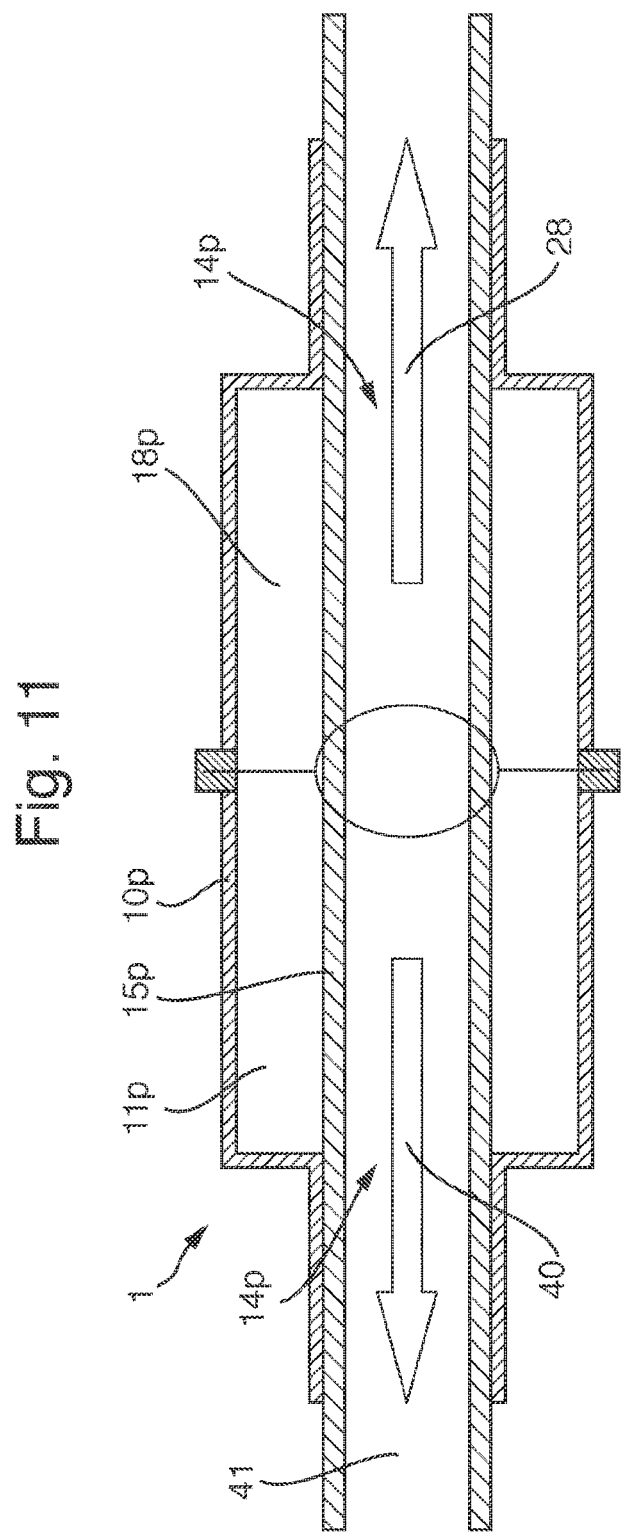

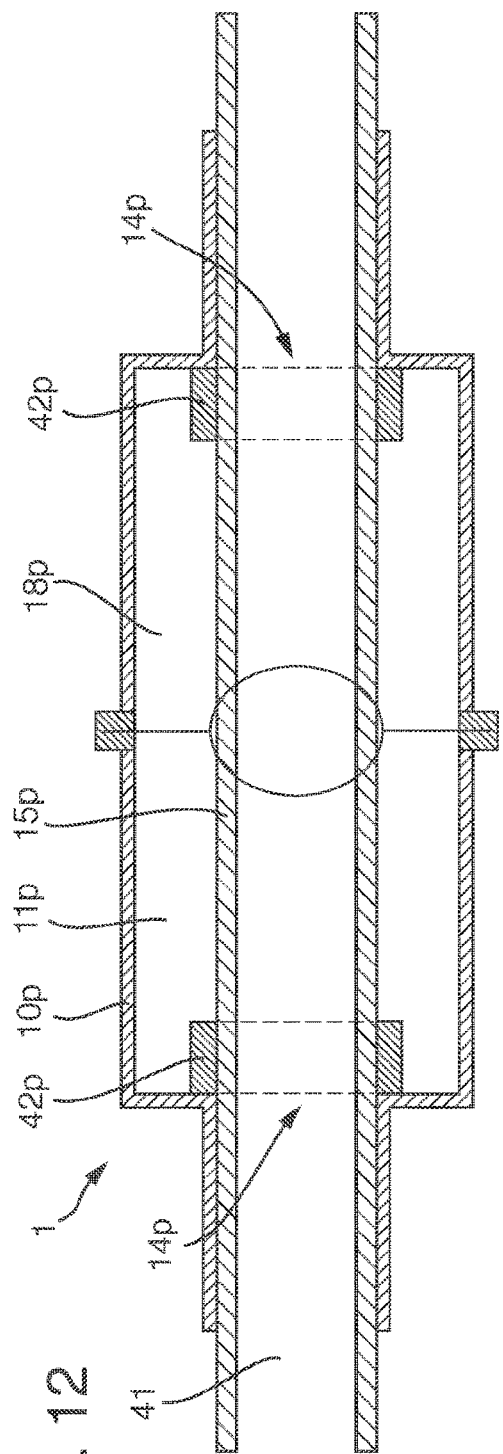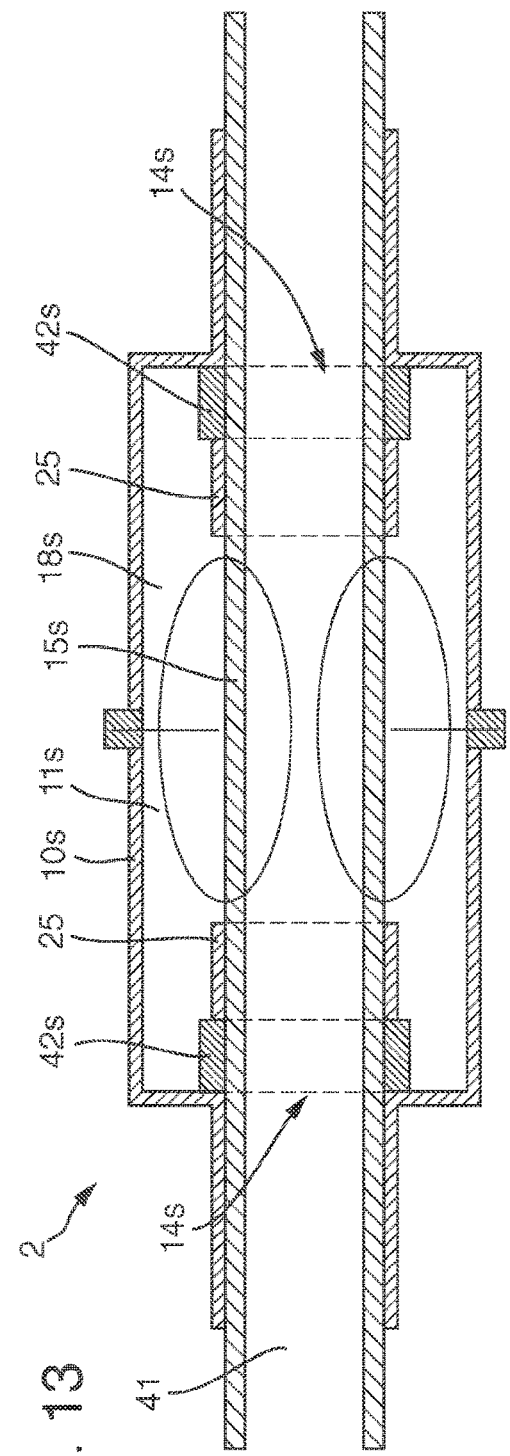

Freq(162)=1.761e9 Multislice: Electric field norm (V/m)

Freq(201)=5e9 Multislice: Electric field norm (V/m)

Freq(201)=5e9 Multislice: Electric field norm (V/m)

Freq(39)=1.76e9 Multislice: Electric field norm (V/m)

CAVITY RESONATOR SYSTEM

BACKGROUND

The present invention relates to a cavity resonator system for measuring electro-magnetic (EM) properties of the contents of a pipe portion, and in particular that can provide compensation for changes in environmental conditions such as temperature and pressure.

Cavity resonators are widely used to measure the dielectric and other EM properties of the contents of a pipe, typically a fluid flowing through the pipe. It is possible to continuously determine, for example, the volume fractions of mineral oil and water emerging from a well, which may be at the surface or subsea. Similarly, the cavity resonator may be used inline with a flow of drilling fluid to measure its water content and salinity. Likewise, the cavity resonator may be deployed inside the Christmas tree at the well-head, or downhole inside a well, to provide in-situ measurements of water cut, water 'hold-up' and salinity.

The cavity is typically formed in an outer conductive casing of metal with the cavity around the pipe completely filled with an insulator material that may be a solid for applications where it is desired to minimize the deformation of the casing under pressure. However, the EM properties of the insulator material change with the environmental conditions such as temperature and pressure, and this can cause significant errors that is variation in the measured response that are not caused by the contents of the pipe under measurement.

For example, one parameter of the resonant EM field in the cavity is a resonance frequency of the cavity. Such a resonance frequency is particularly sensitive to changes in the dielectric properties of the contents of the pipe. However, the resonance frequency is also affected by changes in the cavity dimensions and changes in the permittivity of the insulator material that fills the cavity outside the pipe. Accordingly, it is difficult to determine the dielectric properties of the contents of the pipe from the measured resonance frequency, due to the dependence on the environmental conditions.

One solution would be to attempt to sense the environmental conditions and calibrate the measured parameters on that basis. However, such sensing is impractical in many applications, particularly extreme ones such as are encountered in the petrochemical extraction industry. Furthermore, calibration is difficult to perform accurately.

It would be desirable to tackle errors of this nature in a cavity resonator system used to measure the EM properties of the contents of a pipe portion.

SUMMARY

According to the present invention, there is provided a cavity resonator system for measuring electro-magnetic properties of the contents of a pipe portion, comprising a primary resonator and a secondary resonator each comprising, in the same configuration:

a conductive casing defining a cavity;

insulator material disposed inside the cavity, the casing having a pair of opposed openings for receiving a pipe portion in a configuration extending through the cavity inside the insulator material; and antennae for generating and detecting a resonant electro-magnetic field inside the cavity, the secondary resonator further comprising at least one conductive screening ring that extends around the location to be occupied by a pipe portion received in the openings for screening the interior of the screening ring from a resonant electro-magnetic field generated inside the cavity by an antenna of the secondary resonator.

Accordingly, the present invention makes use of two resonators, each comprising a casing defining a cavity, insulator material and a pair of antennae in the same configuration. The primary resonator may therefore have a similar construction to some existing cavity resonators.

The secondary resonator further comprises at least one conductive screening ring that extends around the location to be occupied by a pipe portion received in the openings. As a result, the interior of the screening ring is screened from a resonant EM field generated inside the cavity by an antenna of the secondary resonator. This means that the response of the secondary resonator is affected by the contents of the pipe portion to a lesser extent than the response of the primary resonator.

However, due to the configuration of the primary and secondary resonators otherwise being the same, the responses of the primary and secondary resonators are affected to the same extent by the EM properties of the other elements of the resonators, such as the cavity shape and dimensions and the EM properties of the insulator material. These EM properties vary in the same manner with changes in the environmental conditions. Since the responses of the primary and secondary resonators are affected by the contents of the pipe portion to differing extents, measures of parameters from the primary and secondary resonators may be combined in a manner that generates a compensated measure representative of EM properties of the contents of a pipe portion, and that reduces the dependence on the EM properties outside the pipe portion, therefore compensating for changes outside the pipe portion.

This cavity resonator system may be applied to pipes having various contents, and the measured parameters of the resonant EM fields in the cavities may be selected to be parameters that are dependent on EM properties that are useful in providing information about the contents. Typical parameters may include the resonance frequency, or parameters that are dependent on losses in the cavity, for example the resonance bandwidth $\Delta\Omega$, or the Q-factor.

The cavity resonator system may be applied to perform measurements on a pipe portion whose contents are a mixture of water and hydrocarbons, such as oil. In that case, the measured parameters may include the resonance frequency of the resonant EM fields in the respective cavity, and a parameter that is dependent on the losses inside the cavity. As a result, a measure of the percentage of water in the pipe portion may be generated from the compensated measure that is itself generated from the measures of resonance frequency, because the property of the contents of the pipe portion that most affects resonance frequency is that percentage. Furthermore, a measure of the salinity of the water in the pipe portion may be generated from the compensated measure that is itself generated from the measures of the parameter that is dependent on the losses inside the cavity. This is because the losses of the contents of the pipe portion are affected by the salinity. The losses are also affected by the percentage of water, and so the generated measure of the percentage of water in the pipe portion is also taken into account.

BRIEF DESCRIPTION OF THE DRAWINGS

Embodiments of the present invention will now be described by way of non-limitative example with reference to the accompanying drawings, in which:

FIG. 1 is a cross-sectional view of a primary resonator of a cavity resonator system;

FIG. 2 is a cross-sectional view of a secondary resonator of the cavity resonator system;

FIG. 5 is diagram of an electrical circuit of the cavity resonator system;

FIG. 6 is a diagram of the response of a resonator;

FIG. 7 is a diagram of an alternative electrical circuit of the cavity resonator system;

FIG. 8 is a cross-sectional view of a cavity resonator system in which the primary and secondary resonators are integrated;

FIGS. 9 and 10 are a cross-sectional views of the primary resonator and secondary resonator, respectively, modified to form the pipe portion integrally with the insulator material;

FIG. 11 is a cross-sectional view of the primary resonator showing RF leakage;

FIG. 12 is a cross-sectional view of the primary resonator modified to include absorbing elements;

FIG. 13 is a cross-sectional view of the secondary resonator of FIG. 3 modified to include absorbing elements;

DETAILED DESCRIPTION

Figure 3:
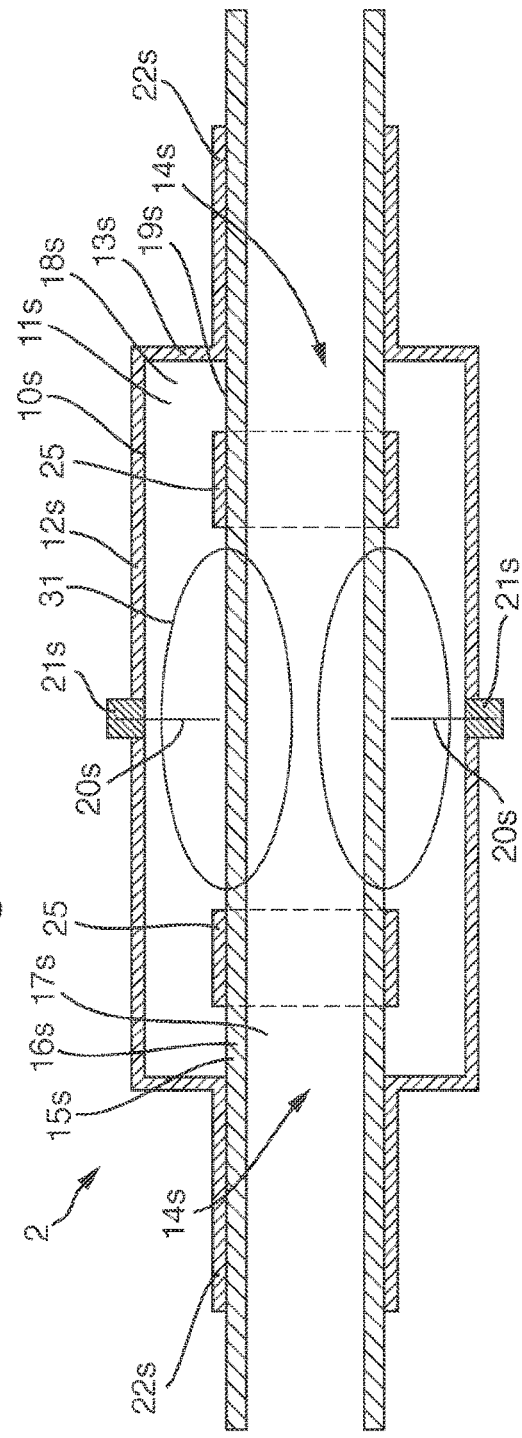
FIG. 3 is a cross-sectional view of a secondary resonator with modified screening rings.

A cavity resonator system comprises a primary resonator 1 as shown in FIG. 1 and a secondary resonator 2 as shown in FIG. 2. The primary resonator 1 and secondary resonator 2 comprise several components having the same configuration. For clarity, such components having the same configuration will herein be given the same reference numeral with a suffix of s or p to distinguish components of the primary resonator 1 and secondary resonator 2.

The primary resonator 1 will now be described.

The primary resonator 1 comprises a casing 10p defining a cavity 11p. The casing 10p is electrically conductive, typically being made of metal. The casing 10p is generally cylindrical, comprising a cylindrical wall 12p and end walls 13p that close the ends of the cylindrical wall 12p.

The end walls 13p have a pair of opposed openings 14p that are aligned along the cylindrical axis of the cylindrical wall 12p. In use, the primary resonator 1 is mounted on a pipe portion 15p by means of the openings 14p receiving the pipe portion 15p. When the primary resonator 1 is so mounted, the openings 14p hold the pipe portion 15p in a configuration extending through the cavity 11p spaced from the cylindrical wall 12p. Outside the openings 14p, the primary resonator 1 has collars 22p for engaging the pipe portion 15p.

In the example shown in FIG. 1, the casing 10p is formed as a continuous piece entirely enclosing the cavity 11p except for the openings 14p. However, the casing 10p could alternatively be made from multiple pieces and/or have apertures that are sufficiently small relative to the EM wavelength to prevent leakage of the EM field.

The pipe portion 15p has an outer wall 16p and a bore 17p for flow of contents therethrough. The outer wall 16p may in general have any construction that is suitable for carrying the contents of the pipe. For example, the outer wall 16p may be formed from a plastic.

The primary resonator 1 further comprises insulator material 18p disposed inside the cavity 11p. Due to the space between the cylindrical wall 12p and the pipe portion 15p when received in the openings 14p, the pipe portion 15p extends through the cavity 11p inside the insulator material 18p.

The insulator material 18p may be solid in which case it has a channel 19p aligned with the openings 14p of the casing 10p. Thus the channel 19p receives a pipe portion 15p received in the openings 14p. An insulator material 18p that is solid may provide the advantage of minimizing deformation of the casing 10p under external pressure, and thus facilitates use in relatively extreme environments, for example undersea. In this case, the insulator material 18p may be any material selected to provide the desired degree of resilience. One possibility suitable for undersea and other applications is for the insulator material 18p to be polyether ether ketone (PEEK).

However, the insulator material 18p may alternatively be a liquid or a gas. In that case a seal may be provided around the openings 14p, particularly for applications where insulator material 18p is different from the surrounding gas or fluid.

The primary resonator 1 further comprises a pair of antennae 20p positioned on opposite sides of the cavity 11p. The antenna 20p are each mounted in the cylindrical wall 12p in respective connectors 21p that electrically insulate the antennae 20p from the cylindrical wall 12p. In use, the casing 10p is grounded, and there is a potential difference between the casing and the antennae 20p.

As described further below, one of the antennae 20p is used to generate a resonant EM field inside the cavity 11p, that is typically a radio-frequency resonant EM field, and the other one of the antennae 20p is used to detect that resonant EM field. In many applications, the wavelength of the EM radiation exceeds the cut-off wavelength of the openings 14p so that the EM radiation is unable to escape down the pipe. The resonant EM field has modes defined by the configuration of the cavity 11p, typically having the greatest field strength in the center of the cavity 11p, for example in the region 30. Thus, the resonant EM field interacts with the contents of the cavity 11p, being the contents of the pipe portion 15p in the bore 17p, the walls 16p of the pipe portion 15p, and the insulator material 18p outside the pipe portion 15p.

The secondary resonator 2 comprises elements 10s to 22s that have the same configuration as the respective elements 10p to 22p of the primary resonator 1. In this context, the "same" configuration includes the physical arrangement and the material properties and means that the elements provide a resonant EM field having the same dependence on the EM properties of those elements for the purpose of comparing measured parameters of the resonant EM field in the cavities 11p and 11s as described further below.

In addition, the secondary resonator 2 comprises two screening rings 25 arranged as follows. The screening rings 25 extend around the location occupied by the pipe portion 15s received in the openings 14s. The screening rings 25 are made from a conductive material and therefore screen their own interiors from the resonant EM field generated inside the cavity 11s of the secondary resonator 2. Thus, in use, the pipe portion 15s inside the screening rings, including the contents of the pipe portion 15s is screened. This means that the response of the secondary resonator 2 is affected by the contents of the pipe portion 15s to a lesser extent than the response of the primary resonator 1. Thus, the resonant EM field in the cavity 11s typically has the greatest field strength outside the screening rings 25, for example in the region 31.

However, due to the configuration of the primary resonator 1 and the secondary resonator 2 otherwise being the same, their responses are affected to the same extent by the EM properties of the other elements of the primary resonator 1 and the secondary resonator 2, such as the shape and dimensions of the cavities 11p an 11s and the EM properties of the insulator material 18p and 18s. These EM properties vary in the same manner as between the primary resonator 1 and the secondary resonator 2 with changes in the environmental conditions.

Since the responses are affected by the contents of the pipe portions 15s and 15p to differing extents, measures of the same parameter taken from the primary resonator 1 and the secondary resonator 2 may be combined in a manner that compensates for changes outside the pipe portions 15p and 15s. This allows the combination to generate a compensated measure that is representative of EM properties of the contents of the pipe portion 15p and 15s. Further details, and the electrical circuit for achieving this, are described below.

In the construction shown in FIG. 2, the screening rings 25 each have the same configuration and are arranged with mirror symmetry about the mid-point between the openings 14s of the casing 10s of the secondary resonator 2. In the direction between the openings 14s of the casing 10s, each has an extent that is less than half the length of the cavity 11s, so that they together have a total extent less than the length of the cavity 11s.

In general, there could be any number of one or more screening rings 25, but the symmetrical arrangement provides the advantage of assisting in the formation of EM modes of the resonant EM field.

Figure 4:
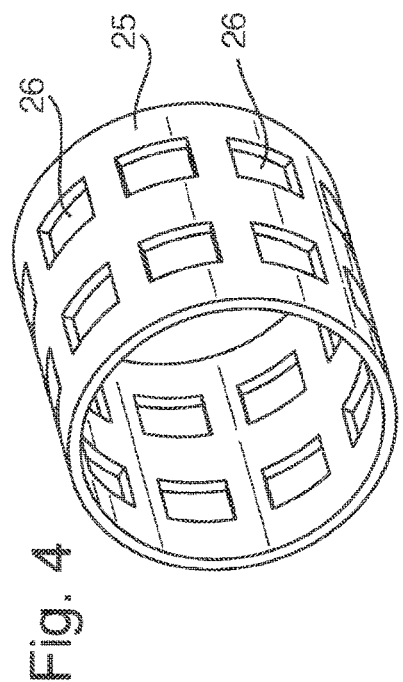
FIG. 4 is a perspective view of a screening ring having apertures.

In general, the total extent of the screening rings 25 the direction between the openings 14s of the casing 10s could vary. The total extent of the screening rings 25 could be the entire length of the cavity 11s, in which case the entirety of the pipe portion 15s inside the cavity 11s would be screened. That would simplify the calculation of a compensated measure that is representative of EM properties of the contents of the pipe portion 15p and 15s. However, greater sensitivity can be achieved by the total extent of the screening rings 25 being lower, because then the overall EM properties of the primary resonator 1 and the secondary resonator 2 are more similar, and the effect of the screening rings 25 is merely a perturbation, but nonetheless dependent on the EM properties of the contents of the pipe portion 15p and 15s. By way of example, FIG. 4 shows the secondary resonator 2 with modified screening rings 25 that have a lesser extent between the openings 14s to achieve this effect.

In FIG. 2, the screening rings 25 are continuous sheets, but they may have any construction which provides screening of their interiors. Thus, as an alternative the screening rings 25 may have apertures. FIG. 3 shows an example of a screening ring 25 having apertures 26 that may be used in the secondary resonator 2. With such apertures 26, the screening ring 25 still screens its interior from the resonant EM field, because the apertures are small relative to the EM wavelength which is of the order of an overall dimension of the cavity 11s.

A possible electrical circuit 50 of the cavity resonator system connected to the primary resonator 1 and the secondary resonator 2 is shown in FIG. 5 and will now be described.

The electrical circuit 50 comprises a drive circuit 51 connected to a first one of the antennae 20p and 20s of each of the primary resonator 1 and the secondary resonator 2, which therefore acts as transmitting antennae. The drive circuit 51 is arranged to drive the antennae 20p and 20s to generate a resonant EM field inside the respective cavities 11p and 11s. The drive circuit 51 may generate a resonant EM field that can be varied across a range of frequencies. The frequency range of the resonant EM field is chosen for the application of the cavity resonator system and the primary resonator 1 and the secondary resonator 2 are designed to support modes in such frequencies, typically to support a single mode such as the TE111 mode. In general, the EM field may be a radio-frequency which may be considered to be a frequency within the range from 1 MHz to 100 GHz. For many applications, the EM field may in a range having a lower limit of 1 MHz, 10 MHz, or 100 MHz and having an upper limit of 10 GHz or 100 GHz.

As an alternative, separate drive circuits could be provided for each of the primary resonator 1 and the secondary resonator 2. However, the provision of a single drive circuit 51 with appropriate splitting circuitry provides the advantage of generating the same resonant EM field in each respective cavity 11p and 11s, reducing the risk of creating a systematic error between them.

The electrical circuit 50 further comprises an analysis circuit 52 connected to a second one of the antennae 20p and 20s of each of the primary resonator 1 and the secondary resonator 2, which therefore acts as receiving antennae. In this embodiment, the analysis circuit 52 comprises two spectrum analyzers 53 each connected to one of the primary resonator 1 and the secondary resonator 2, and each arranged to derive a measure of at least one parameter of the resonant EM field in the respective cavity 11p and 11s.

The parameter, or each parameter where there is more than one, is a parameter that is dependent on EM properties of the contents of the respective cavity and is therefore useful for sensing the EM properties of the contents of the pipe portions 15p and 15s. Preferably, at least two parameters of the resonant EM field that are dependent on different EM properties are selected to provide increased information.

To illustrate some parameters that may be selected, a typical frequency response of a cavity is shown in FIG. 6 which is a graph showing how the amplitude of the resonant EM field varies with its frequency ω. The spectrum analyzers 53 measure the response across a range of frequencies and derive the parameters therefrom, in a conventional manner. Thus the spectrum analyzers 53 are connected to the drive circuit 51 to obtain information about the frequency at any given time.

One parameter that may be selected is the resonance frequency ω0, i.e. the frequency at which the amplitude of the response is maximum. The resonance frequency ω0 is not substantially affected by losses in the cavity. If the cavity is modeled as a parallel resistance R, inductance L and capacitance C, then the resonance frequency $\omega 0=1/\sqrt{(LC)}$ which is not dependent on R which represents the losses in the cavity.

Other parameters that may be selected include parameters that are dependent on the losses inside the cavity. Suitable parameters, and their RLC representation if the cavity is modeled as a parallel resistance R, inductance L and capacitance C are: the resonance bandwidth $\Delta\omega=1/(RC)$; or the Q-factor $Q=R\sqrt{(C/L)}$, which are both dependent on R which represents the losses in the cavity. The resonance bandwidth Δω is the 3 dB bandwidth.

Parameters may similarly be derived from the phase response.

In respect of the parameter, or each parameter where there is more than one, the measures of the parameter are output from spectrum analyzers 53 to a processing circuit 54 which further processes the measures of each parameter as follows.

The processing circuit 54 may be any form of circuit that is capable of performing the processing, for example a microprocessor running an appropriate program.

The processing circuit 54 combines the measures of the parameter derived in respect of the primary resonator 1 and the secondary resonator 2 to generate a compensated measure representative of EM properties of the contents of the pipe portions 15s and 15p that removes, or at least reduces, the dependence of the parameter on the EM properties outside the pipe portion, therefore compensating for the effect of changes in the environmental conditions, as compared to use of the primary resonator 1 by itself. This is possible because the EM properties of the primary resonator 1 and the secondary resonator 2 outside the pipe portions 15p and 15s are the same.

The nature of the combination the measures of the parameter derived in respect of the primary resonator 1 and the secondary resonator 2 depends on the parameter itself, but can be derived from a consideration of the EM properties of the cavities 11p and 11s. Some examples will now be given.

In the case that parameter is the resonance frequency $\omega 0$, then modeling the cavities 11p and 11s as a parallel resistance R, inductance L and capacitance C, the resonance frequency $\omega 0 = 1/\sqrt{(LC)}$. In this case, in typical applications the difference in the EM properties between the primary resonator 1 and the secondary resonator 2 causing difference in the resonance frequency $\omega 0$ is primarily the difference in the capacitance $\delta C$ caused by the screening of the interior of the screening rings 25 in the secondary cavity 11s. In typical applications the difference in the inductance will be zero, or at least insignificant as the contents of the pipe portions 15s and 15p will not be inductive. The capacitance will be greater in the primary resonator 1, which may be viewed in terms of capacitance of the primary resonator 1 being dependent on a greater volume of dielectric in the pipe portion 15p due to the screening in the secondary resonator 2. The difference in the capacitance $\delta C$ is dependent solely on the pipe portions 15s and 15p, and in particular on the permittivity of the contents of the pipe portions 15s and 15p.

Thus, if the resonance frequency $\omega 0s$ of the secondary resonator 2 is given by $\omega 0s = 1/\sqrt{(L.Cs)}$, where Cs is the capacitance of the secondary resonator 2, then the resonance frequency $\omega 0p$ of the primary resonator 1 is given by $\omega 0p = 1/\sqrt{(L.(Cs+\delta C))}$. These equations for the resonance frequencies $\omega 0s$ can be solved analytically to derive the difference in the capacitance $\delta C$.

A simpler solution can be derived based on the observation that in typical applications the difference in the capacitance $\delta C$ is significantly less than the capacitance Cs. In that case, based on a Taylor expansion of $\omega 0p = 1/\sqrt{(L.(Cs+\delta C))}$, it can be seen that the first term in the difference in the resonance frequencies $(\omega 0p - \omega 0s)$ is proportional to the difference in the capacitance $\delta C$. Accordingly, to first order, the difference in the resonance frequencies $(\omega 0p - \omega 0s)$ provides a compensated measure of the difference in the capacitance $\delta C$, which is also a measure of the permittivity of the contents of the pipe portions 15s and 15p. Thus, in the case of using measures of the resonance frequency $\omega 0$, the processing circuit 54 may combine the measures of the resonance frequencies $\omega 0p$ and $\omega 0s$ by subtracting them.

A consideration of the Taylor expansion similarly shows that the measures of the resonance frequencies $\omega 0p$ and $\omega 0s$ may be combined by dividing them, which again provides a measure of the difference in the capacitance $\delta C$, which is also a measure of the permittivity of the contents of the pipe portions 15s and 15p.

Modeling of the cavities 11p and 11s has been performed to illustrate the viability of this correction process when using of the parameter of the resonance frequency $\omega 0$, as follows.

The modeling gives values of the resonance frequency $\omega 0$ that are shown in the following tables. The permittivity of the fluid that forms the contents of the pipe portions 15s and 15p takes one of three values 2.0, 2.2 and 2.4, that are typical values for different fluids. The insulator material 18p and 18s is taken to be a plastic whose permittivity changes with takes one of three values 3.0, 3.3 and 3.6 that are typical for changes with environmental conditions. The resonance frequency $\omega 0$ of the TE111 mode in the primary resonator has been calculated to the nearest 1 MHz to have the following values in the primary resonator 1.

| Primary resonator 1 (±1 MHz) | | | |
|---|---|---|---|
| | Fluid $\epsilon$ = 2.0 | Fluid $\epsilon$ = 2.2 | Fluid $\epsilon$ = 2.4 |
| Plastic $\epsilon$ = 3.0 | 1.847 GHz | 1.819 GHz | 1.793 GHz |
| Plastic $\epsilon$ = 3.3 | 1.788 GHz | 1.761 GHz | 1.736 GHz |
| Plastic $\epsilon$ = 3.6 | 1.734 GHz | 1.709 GHz | 1.685 GHz |

As expected, the resonance frequency $\omega 0$ of the primary resonator 1 shifts as either the permittivity of the fluid changes or the permittivity of the plastic changes.

The resonance frequency $\omega 0$ of the lowest-frequency mode in the secondary resonator 2 is now calculated for the same permittivity values again to the nearest 1 MHz to have the following values.

| Secondary resonator 2 (±1 MHz) | | | |
|---|---|---|---|
| | Fluid $\epsilon$ = 2.0 | Fluid $\epsilon$ = 2.2 | Fluid $\epsilon$ = 2.4 |
| Plastic $\epsilon$ = 3.0 | 1.263 GHz | 1.262 GHz | 1.262 GHz |
| Plastic $\epsilon$ = 3.3 | 1.204 GHz | 1.204 GHz | 1.204 GHz |
| Plastic $\epsilon$ = 3.6 | 1.153 GHz | 1.153 GHz | 1.153 GHz |

This shows that the resonance frequency $\omega 0$ of the secondary resonator 2 is virtually independent of the permittivity of the fluid, but still changes as the permittivity of the plastic changes.

The differences in the resonance frequencies $(\omega 0p - \omega 0s)$ are calculated to have the following values.

| Difference in the resonance frequencies $(\omega_0 p - \omega_0 s)$ (±2 MHz) | | | |
|---|---|---|---|
| | Fluid $\epsilon$ = 2.0 | Fluid $\epsilon$ = 2.2 | Fluid $\epsilon$ = 2.4 |
| Plastic $\epsilon$ = 3.0 | 584 MHz | 557 MHz | 531 MHz |
| Plastic $\epsilon$ = 3.3 | 584 MHz | 557 MHz | 532 MHz |
| Plastic $\epsilon$ = 3.6 | 581 MHz | 556 MHz | 532 MHz |

This shows that the difference in the resonance frequencies $(\omega 0p - \omega 0s)$ provide a measure that is representative of the permittivity of the fluid regardless of changes in the permittivity of the plastic. Thus, the difference frequency provides a more accurate measure of the fluid properties that is virtually independent of any changes in the permittivity of the plastic.

The nature of the combination in the case that parameter is the Q-factor will now be considered, as an example of a parameter that is dependent on the losses inside the cavity. Modeling the cavities 11p and 11s as a parallel resistance R, inductance L and capacitance C, the Q-factor $Q = R\sqrt{(C/L)}$.

In this case, in typical applications the difference in the EM properties between the primary resonator 1 and the secondary resonator 2 causing difference in the Q-factor is primarily the additional resistance δR caused by the screening of the interior of the screening rings 25 in the secondary cavity 11*s*. As discussed above with reference to the resonance frequency ω0, there is a difference in the capacitance δC, but it is observed that this typically causes significantly less effect on the Q-factor than the difference in resistance δR. In typical applications the difference in the inductance will be zero, or at least insignificant as the contents of the pipe portions 15*s* and 15*p* will not be inductive.

The additional resistance δR in the primary resonator 1 will be arranged in parallel with the resistance Rs of the secondary resonator 2. This may be viewed in terms of resistance of the primary resonator 1 being dependent on a greater volume of fluid in the pipe portion 15*p* due to the screening of at least some of the contents of the pipe portion 15*s* in the secondary resonator 2. Another way to view this is that the screening rings 25 reduce the losses seen by the secondary resonator 2 causing an apparent increase in the primary resonator 1 compared to the secondary resonator 2. The additional resistance δR is dependent solely on the pipe portions 15*s* and 15*p*, and in particular on the overall conductance of the contents of the pipe portions 15*s* and 15*p*, which creates losses in the cavities 11*p* and 11*s*.

If the Q-factor Qs of the secondary resonator 2 is given by Qs=Rs√(C/L), then the Q-factor Qp of the primary resonator 1 is given by Qp=((Rs.δR)/(Rs+δR)).√(C/L). These equations for the Q-factor Qs and Qp can be solved analytically to derive the additional resistance δR, giving a formula δR, (Qs.Qp/(Qs−Qp)).√(L/C). Thus, in the case of using measures of the Q-factor, the processing circuit 54 may combine the measures of the Q-factor Qs and Qp in accordance with this formula to generate a compensated measure of the additional resistance δR, which is also a measure of the overall conductance of the contents of the pipe portions 15*s* and 15*p*.

A similar approach may be applied for other parameters such as the resonance bandwidth Δω.

The cavity resonator system may have applications in a variety of fields with pipes carrying a variety of contents.

One field of particular interest is the petrochemical industry, where the cavity resonator system may be applied in exploration, production or downstream. For example, the cavity resonator system may be used to measure hydrocarbons and water emerging from a well, which may be at the surface or subsea. Similarly, the cavity resonator system may be used inline with a flow of drilling fluid to measure its water content and salinity. Likewise, the cavity resonator system may be deployed inside the Christmas tree at the well-head, or downhole inside a well, to provide in-situ measurements of water cut, water 'hold-up' and salinity.

One type of pipe contents of interest is fluids comprising a mixture of water and hydrocarbons, such as oil, particularly where oil is the continuous phase. For example, this could be where there are droplets of water suspended in a continuous oil matrix. In this case, both the percentage of water and its salinity may be of interest.

In an example where the cavity resonator system is for measuring a pipe portion carrying a mixture of water and hydrocarbons, the analysis circuit 52 may operate as follows to provide a measure of the percentage of the water and the salinity.

In this example, the parameters derived by the spectrum analyzers 53 may be the resonance frequency ω0 of the resonant EM fields in the cavities 11*p* and 11*s*, and a parameter that is dependent on the losses inside the cavities 11*p* and 11*s*, for example the Q-factor or the resonance bandwidth Δω.

In respect of the parameter of the resonance frequency ω0, the processing circuit 54 generates a compensated measure of representative of the EM properties of the contents of a pipe portions 15*s* and 15*p* that is a measure of the difference in the capacitance δC, as described above. This measure is also a measure of the permittivity of the contents of the pipe portions 15*s* and 15*p*. In the case of carrying a mixture of water and hydrocarbons, the permittivity of the water is different from the permittivity of the hydrocarbons. On this basis, the processing circuit 54 generates a measure of the percentage of water in the pipe portions 15*p* and 15*s* from this compensated measure of the difference in the capacitance W.

In respect of the parameter that is dependent on the losses, the processing circuit 54 generates a compensated measure of representative of the EM properties of the contents of a pipe portions 15*s* and 15*p* that is a measure of the additional resistance δR, and so a measure of the losses, as described above. This measure is also a measure of the overall conductance of the contents of the pipe portions 15*s* and 15*p*. In the case of carrying a mixture of water and hydrocarbons, the conductivity of the water is significantly greater than from the conductivity of the hydrocarbons, and the conductivity of the water is dependent on the salinity of the water. Thus the overall conductance is proportional to the percentage of water and dependent on the salinity of the water. On this basis, the processing circuit 54 generates a measure of the conductivity of the water in the pipe portions 15*p* and 15*s* from this compensated measure of the additional resistance δR, taking into account measure of the percentage of water in the pipe portions 15*p* and 15*s* generated using the measured parameter of the resonance frequency ω0 as above.

The location of the primary resonator 1 and the secondary resonator 2 on respective pipe portions 15*s* and 15*p* will now be discussed. As well as the primary resonator 1 and the secondary resonator 2 having the same configuration, they are preferably mounted on pipe portions 15*s* and 15*p* that carry a common flow of fluid. The pipe portions 15*s* and 15*p* may be arranged in series or in parallel with respect to that flow.

The temperature of the contents of the pipe portions 15*s* and 15*p* is a major factor in the environmental conditions that affect the EM properties of the primary resonator 1 and the secondary resonator 2. Thus, causing the primary resonator 1 and the secondary resonator 2 to be affected by a common flow of fluid causes their responses to be affected to the same extent by the variance in their EM properties caused by the contents of the pipe portions 15*p* and 15*s*, thereby improving the compensation effect.

To provide pipe portions 15*p* and 15*s* in series, the pipe portions 15*p* and 15*s* may be portions of the same pipe. An example of this where the primary resonator 1 and the secondary resonator 2 are integrated together is shown in FIG. 8. In this example, the primary resonator 1 and the secondary resonator 2 have the same construction as described above, except that the casings 10*p* and 10*s* have a common end wall 23. As a result, the openings 14*p* and 14*s* of the primary resonator 1 and the secondary resonator 2 are aligned and receive pipe portions 15*p* and 15*s* that are portions of the same pipe 27.

For many applications, the primary resonator 1 and the secondary resonator 2 may be fitted to pipe portions 15*p* and 15 *s* that are manufactured separately from the primary resonator 1 and the secondary resonator 2. In that case, the primary resonator 1 and the secondary resonator 2 may be fitted in situ on pipe portions 15p and 15s that are portions of the same or different pipe.

For other applications, the primary resonator 1 and the secondary resonator 2 may be manufactured together with the pipe portions 15p and 15s. Then, the pipe portions 15p and 15s may be connected into a pipe system for flow of contents through the pipe portions 15p and 15s. Where the primary resonator 1 and the secondary resonator 2 are manufactured together with the pipe portions 15p and 15s, the walls 16p and 16s of the pipe portions 15p and 15s may be separate pieces of material from the insulator material 18p and 18s, for example as shown in FIGS. 1 to 3 and 8. As an alternative, the pipe portions 15p and 15s and the insulator material 18p and 18s may be integrated, for example by the walls 16p and 16s of the pipe portions 15p and 15s being formed integrally with the insulator material 18p and 18s. FIGS. 9 and 10 shows an example of the primary resonator 1 and the secondary resonator 2 modified in this manner.

Loss of EM energy along the pipe of in which the pipe portions 15p and 15s are formed will now be considered.

In many applications, the wavelength of the resonant EM field is sufficiently long compared to the size of the openings 14p and 14s that EM energy is not lost along the pipe outside the pipe portions 15p and 15s. For example, in an application for a pipe carrying a mixture of mineral oil and water, measurements performed at frequencies below 1.5 GHz have a sufficiently large wavelength to prevent leakage of the EM energy down pipes of up to 10 cm in diameter. The EM energy is confined to the resonator, increasing the resonant Q factor of the cavity and improving the accuracy of the measurement.

However, in other applications, the wavelength of the resonant EM field may be lower to an extent that permits leakage of the EM energy down along the pipe outside the pipe portions 15p and 15s. For example, in an application for a pipe carrying a mixture of mineral oil and water emerging from an undersea well, more information can be obtained on the fluid properties if measurements are performed at higher frequencies above 3 GHz. This is because the dielectric properties of water are largely independent of frequency below 3 GHz but change significantly with frequency at higher values. By making measurements at multiple frequencies above 3 GHz, the volume fractions of mineral oil and water can be determined with greater accuracy. However, in this application, the wavelength at 10 GHz is sufficiently small to allow leakage of EM energy down relatively small pipes, even with diameters smaller than 1 cm.

To illustrate this, FIG. 11 illustrates the primary resonator 1 of FIG. 1 wherein the arrows 40 shows the loss of EM energy from the pipe portion 15p into the remainder of the pipe 41.

One solution to this is to place metallic grids with apertures within the pipe at each end of the cavities 15p and 15s. The size of the apertures is chosen to allow fluid to flow easily through the apertures but to trap EM energy is trapped inside the cavities 15p and 15s. However, in a crude oil application this is not practical as the grids will rapidly get clogged or be destroyed by the flowing liquid. One possible way to tackle this is to make a wider but deeper grid. The cut off frequency of the wider apertures may be a low multiple of the mode frequency so there is a significant evanescent wave compared to a grid with small holes. Therefore, the grid may be made thicker so that the evanescent wave has a longer distance to decay over and very little EM energy escapes the cavities 15p and 15s. Also, a grid that has bigger apertures and is thicker is less of a restriction to the flow and is likely to last longer than a thin, small-holed grid.

An alternative solution is to provide the cavities 15p and 15s with absorbing elements that absorb EM energy that would otherwise leak through the openings 14p and 14s. As an example of this solution, FIGS. 12 and 13 illustrate the primary resonator 1 and the secondary resonator 2 in which such absorbing elements 42p and 42s are provided, as follows.

The primary resonator 1 additionally comprises annular absorbing elements 42p that are positioned adjacent the openings 14p and extending around the openings 14p. In this example, the absorbing elements 42p are provided inside the cavity 11p, but they could alternatively be provided outside the cavity 11p. The absorbing elements 42p could alternatively be incorporated as flanges, washers, gaskets, O-rings, seals, coatings, films, embedded wire or sections of pipe, for example. The absorbing elements 42p are arranged to absorb EM energy and thereby reduce the amount of EM energy exiting from the cavity 11p through the openings 14p.

The absorbing elements 42p may be solid components made from any material that absorbs EM energy at the frequencies used in the cavity resonator system. For example, the material may be a conductive plastic. The material may have a conductivity in the range from 0.1 S/m to 1 S/m. For TE or TM waves to pass down a waveguide the conducting surfaces of the waveguide are preferably good reflectors. Thus, the absorbing elements 42p will drastically reduce the amount of reflected EM energy reflected and this will reduce or prevent the EM waves being transmitted a large distance along the pipe 41 outside the pipe portion 15p. There will be a reduction in the Q-factor of the cavity 11s due to the losses in the absorbing elements 42p but this will be fairly constant despite with variations in the material in the pipe portion 15p and not significant compared to the losses from this material.

The absorbing elements 42p may alternatively be solid components from an EM scattering material, because the destructive interference may be less lossy than absorbing the EM energy. A plastic containing carbon powder or conductive polymers may be used. Another option is to have a manifold of smaller pipes all parallel between the feed pipe and the resonator.

The absorbing elements 42p may alternatively be a material arranged as one or more helical antenna, or a plurality of helical antennae, arranged to transmit and receive EM frequencies so as to contain the field within the cavity 11p.

The secondary resonator 2 comprises absorbing elements 42s having the same configuration as the absorbing elements 42p of the primary resonator 1, and having the same effect on the EM field.

FIGS. 14 to 17 illustrate resonant fields formed in the primary resonator 1 derived from modeling to illustrate the effect of the absorbing elements 42p.

Figure 14:
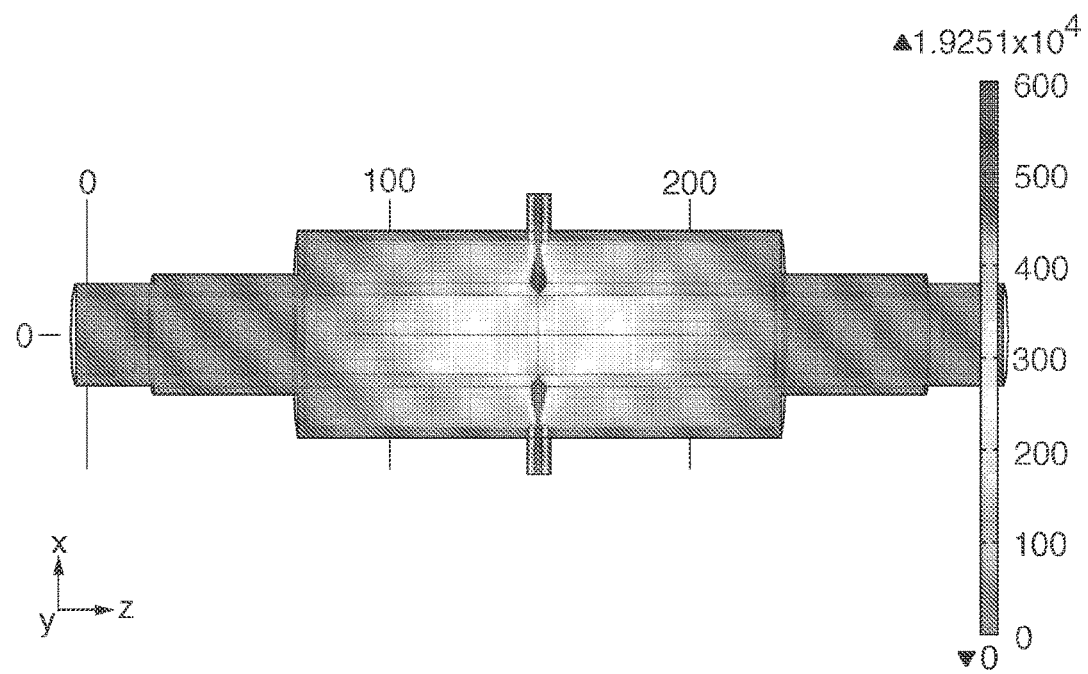
FIGS. 14 to 17 are cross-sectional views of a primary resonator showing different distributions of EM field.

To illustrate an example where there is no loss, FIG. 14 shows the resonant EM field in the primary resonator 1 without absorbing elements 42p used to perform low frequency (up to 3 GHz) measurements of the dielectric properties of a fluid in pipe portion 15p that has a diameter of 25 mm. The resonator is used to determine the resonance frequency of the TE111 mode where the electric field is strongest in the center of the cavity 11p and the resonance frequency is particularly sensitive to changes in the dielectric properties of the contents of the pipe portion 15p. FIG. 14 shows the spatial distribution of the electric field strength at the frequency of the TE111 mode, in this case at 1.761 GHz. The EM energy at this frequency has a wavelength of 7.7 cm and is unable to propagate along the pipe.

Figure 15:
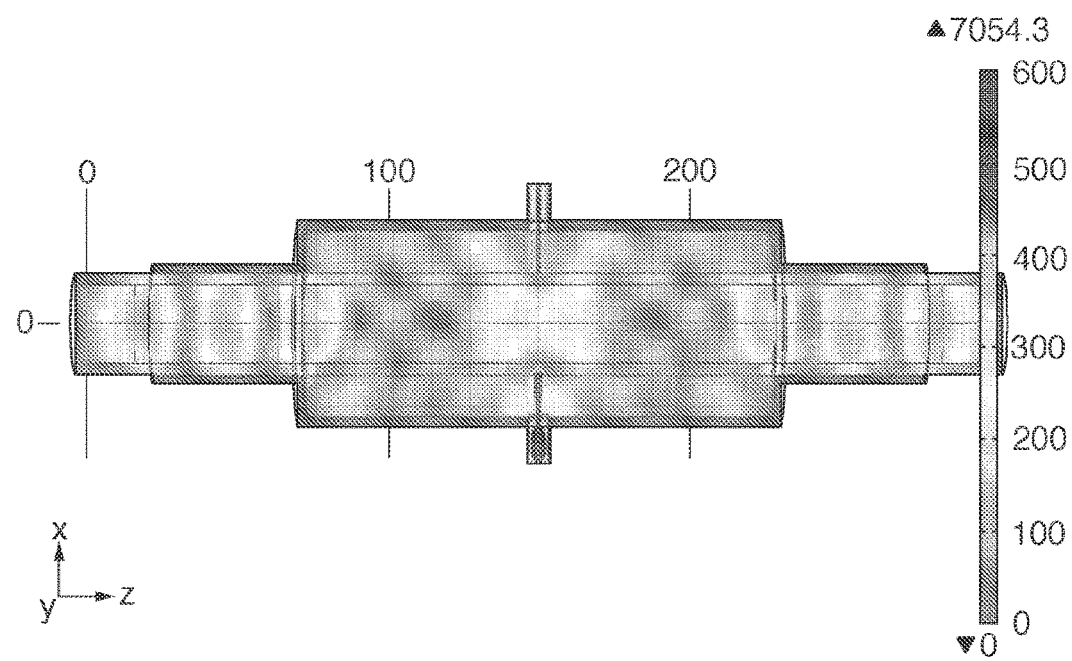

FIG. 15 shows the spatial distribution of the electric field strength in the primary resonator 1 without absorbing elements 42p at a frequency of 5 GHz. The EM energy at this frequency has a wavelength of 2.7 cm and is just able to escape from the cavity 11p along the pipe 41 as shown.

Figure 16:
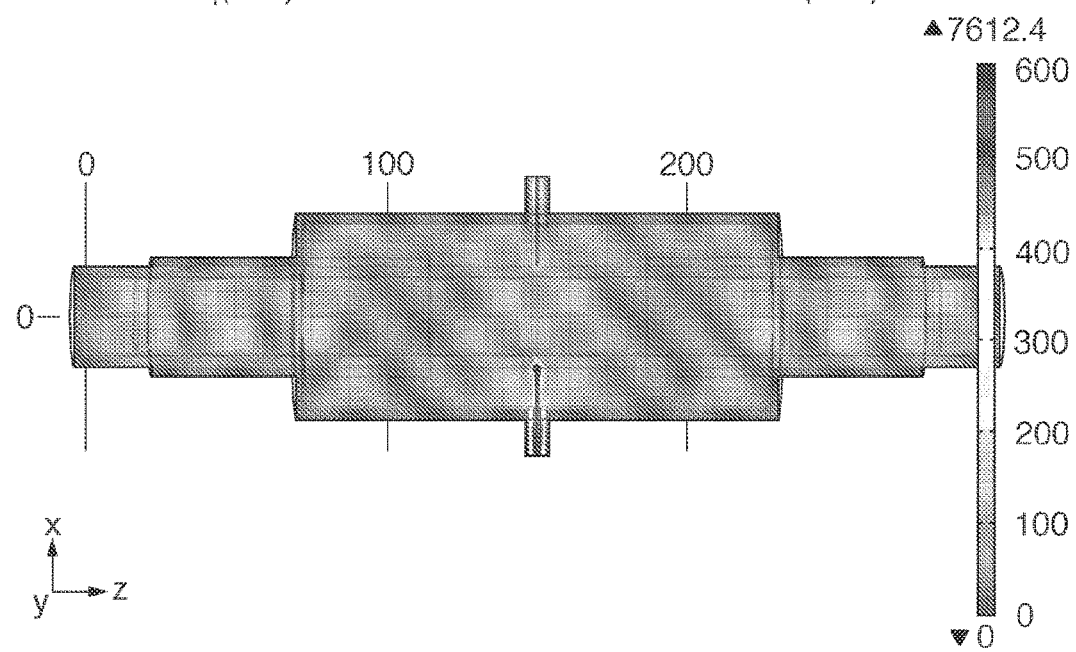

FIG. 16 shows the resonant EM field in the primary resonator 1 including absorbing elements 42p to prevent this leakage. Modeling shows that the conducting plastic formulation should have an electrical conductivity value that falls within the range 0.1 S/m to 1 S/m. FIG. 16 shows the electric field strength in the cavity 11p at a frequency of 5 GHz and illustrates how absorbing elements 42p with an electrical conductivity value of 0.25/m are able to weaken the amount of EM energy leaking down the pipe 41.

With much lower conductivity values, the absorbing elements 42p have a negligible absorbing effect on the EM energy. With much higher conductivity values, the absorbing elements 42p behave like a metal and facilitate the propagation of the EM energy within the pipe 41. The presence of the absorbing elements 42p does have a small perturbing effect on the frequency and strength of the TE111 mode but the effect can be weakened by tailoring the length and electrical conductivity of the absorbing elements 42p.

Figure 17:
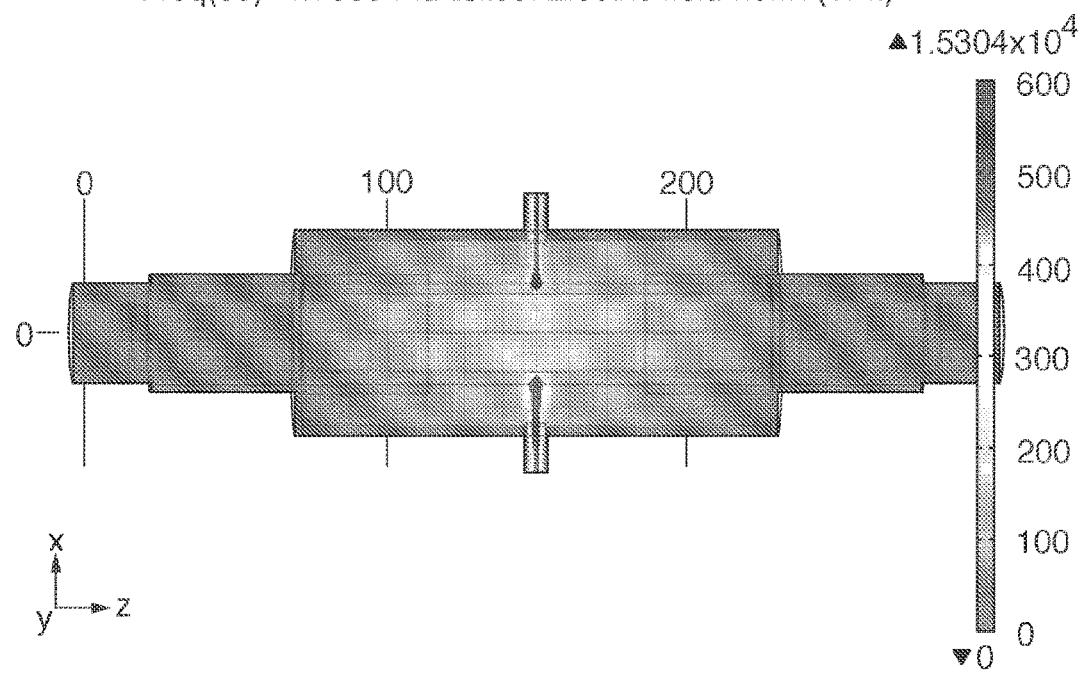

FIG. 17 shows the spatial distribution of the electric field strength in the primary resonator 1 including absorbing elements 42p at the frequency of the TE111 mode, which can be compared with FIG. 14. The resonance frequency was 1.759 GHz, a small shift of 2 MHz from the value of 1.761 GHz observed without the absorbing elements 42p.

Many combinations, modifications, or alterations to the features of the above embodiments will be readily apparent to the skilled person and are intended to form part of the invention. Any of the features described specifically relating to one embodiment or example may be used in any other embodiment by making the appropriate changes.

The invention claimed is:

1. A cavity resonator system for measuring electro-magnetic properties of the contents of a pipe portion, comprising
    a primary resonator and a secondary resonator each comprising, in the same configuration:
    a conductive casing defining a cavity;
    insulator material disposed inside the cavity, the casing having a pair of opposed openings for receiving a pipe portion in a configuration extending through the cavity inside the insulator material; and
    antennae for generating and detecting a resonant electro-magnetic field inside the cavity,
    the secondary resonator further comprising at least one conductive screening ring that extends around the location to be occupied by a pipe portion received in the openings for screening the interior of the screening ring from a resonant electro-magnetic field generated inside the cavity by an antenna of the secondary resonator.

2. A cavity resonator system according to claim 1, wherein, in the direction between the openings of the casing of the secondary resonator, the total extent of the at least one screening ring is less than the length of the cavity.

3. A cavity resonator system according to claim 1, wherein the at least one screening ring comprises plural screening rings.

4. A cavity resonator system according to claim 1, wherein the at least one screening ring is arranged with mirror symmetry about the mid-point between the openings of the casing of the secondary resonator.

5. A cavity resonator system according to claim 1, wherein the at least one screening ring has plural apertures.

6. A cavity resonator system according to claim 1, wherein the insulator material is solid and has a channel aligned with the openings of the casing for receiving a pipe portion received in the openings.

7. A cavity resonator system according to claim 1, wherein the primary resonator and the secondary resonator each further comprise the pipe portion, the pipe portion comprising a wall around a bore, and wherein the insulator material is solid and formed integrally with the wall of the pipe portion.

8. A cavity resonator system according to claim 1, wherein the conductive casing comprises a cylindrical wall and end walls closing the ends of the cylindrical wall, the openings being aligned along the cylindrical axis of the cylindrical wall.

9. A cavity resonator system according to claim 1, wherein the resonant electro-magnetic field is a radio-frequency resonant electro-magnetic field.

10. A cavity resonator system according to claim 1, wherein the primary resonator and the secondary resonator further comprise, in the same configuration, absorbing elements positioned adjacent the openings and extending around openings, the absorbing elements being arranged to absorb electro-magnetic energy and thereby reduce the amount of electro-magnetic energy exiting from the cavity through the openings.

11. A cavity resonator system according to claim 10, wherein the absorbing elements are disposed inside the cavity.

12. A cavity resonator system according to claim 10, wherein the absorbing elements comprise a conductive plastic.

13. A cavity resonator system according to claim 10, wherein the absorbing elements have a conductivity in the range from 0.1 S/m to 1 S/m.

14. A cavity resonator system according to claim 1, wherein the primary resonator and the secondary resonator are integrated together with their openings aligned to receive pipe portions that are portions of the same pipe.

15. A cavity resonator system according to claim 1, wherein the openings of the primary resonator and the openings of the secondary resonator receive respective pipe portions that are arranged in series or in parallel with respect to a flow of fluid.

16. A cavity resonator system according to claim 1, further comprising a pipe for carrying a fluid, the openings of the primary resonator and the openings of the secondary resonator receiving respective pipe portions that are portions of the pipe.

17. A cavity resonator system according to claim 1, further comprising a drive circuit connected to a first antenna of each of the primary resonator and the secondary resonator and arranged to drive the antennae of each of the primary resonator and the secondary resonator to generate a resonant electro-magnetic field inside the respective cavity.

18. A cavity resonator system according to claim 17, further comprising an analysis circuit connected to a second antenna of each of the primary resonator and the secondary resonator, the analysis circuit being arranged:
    to derive, in respect of each of the primary resonator and the secondary resonator, a measure of at least one parameter of the resonant electro-magnetic field in the respective cavity that is dependent on electro-magnetic properties of the contents of the respective cavity, and in respect of the at least one parameter, to combine the derived measures in respect of each of the primary resonator and the secondary resonator to generate a compensated measure representative of electro-magnetic properties of the contents of a pipe portion received in the openings that is compensated for dependence of the parameter on EM properties of the cavity outside the pipe portion.

19. A cavity resonator system according to claim 18, wherein said at least one parameter comprises at least two parameters of the resonant electro-magnetic field in the respective cavity that are dependent on different electro-magnetic properties of the contents of the respective cavity.

20. A cavity resonator system according to claim 18, wherein said at least one parameter includes the resonance frequency of the resonant electro-magnetic fields in the respective cavity.

21. A cavity resonator system according to claim 18, wherein said at least one parameter includes a parameter that is dependent on the losses inside the cavity.

22. A cavity resonator system according to claim 19 for measuring the electro-magnetic contents of a pipe portion whose contents are a mixture of water and hydrocarbons, wherein said at least one parameter includes the resonance frequency of the resonant electro-magnetic fields in the respective cavity, and a parameter that is dependent on the losses inside the cavity, and the analysis circuit is arranged:

- to generate a measure of the percentage of water in the pipe portion from the compensated measure generated from the measures of resonance frequency, and
- to generate a measure of the salinity of the water in the pipe portion from the compensated measure generated from the measures of parameter that is dependent on the losses inside the cavity, taking into account the generated measure of the percentage of water in the pipe portion.

\* \* \* \* \*